(12) United States Patent
Van Kruchten

(10) Patent No.: US 8,569,548 B2
(45) Date of Patent: Oct. 29, 2013

(54) PROCESS FOR THE PREPARATION OF ALKYLENE GLYCOLS

(75) Inventor: Eugene Marie Godfried Andre Van Kruchten, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1260 days.

(21) Appl. No.: 12/176,142

(22) Filed: Jul. 18, 2008

(65) Prior Publication Data

US 2009/0105508 A1    Apr. 23, 2009

(30) Foreign Application Priority Data

Jul. 20, 2007    (EP) ................................... 07112862

(51) Int. Cl.
*C07C 29/10* (2006.01)
(52) U.S. Cl.
USPC .......................................... 568/867; 568/870
(58) Field of Classification Search
USPC ................................................. 568/867, 870
See application file for complete search history.

(56) References Cited

U.S. PATENT DOCUMENTS

| | | | | |
|---|---|---|---|---|
| 4,160,116 A | 7/1979 | Mieno et al. | .................. | 568/867 |
| 4,283,580 A | 8/1981 | Odanaka et al. | .............. | 568/858 |
| 4,307,256 A | 12/1981 | Cipriani et al. | .............. | 568/867 |
| 4,571,440 A * | 2/1986 | Keen et al. | .................... | 568/872 |
| 4,786,741 A * | 11/1988 | Sachs | ............................. | 549/230 |
| 4,982,021 A | 1/1991 | Best et al. | ...................... | 568/867 |
| 5,488,184 A | 1/1996 | Reman et al. | ................. | 568/867 |
| 6,124,508 A | 9/2000 | Van Kruchten | ............... | 568/867 |
| 6,153,801 A | 11/2000 | Van Kruchten | ............... | 568/867 |
| 6,156,942 A | 12/2000 | Lemanski et al. | ............ | 568/867 |
| 7,674,919 B2 * | 3/2010 | Boele et al. | ................... | 549/230 |

FOREIGN PATENT DOCUMENTS

| | | |
|---|---|---|
| EP | 156449 | 10/1985 |
| EP | 1034158 | 5/1999 |
| JP | 56092228 | 7/1981 |
| JP | 57106631 | 7/1982 |
| JP | 57139026 | 8/1982 |
| JP | 59013741 | 1/1987 |
| JP | 09235252 | 9/1997 |
| JP | 2001151711 | 6/2001 |
| JP | 2001151713 | 6/2001 |
| RU | 2149864 | 2/1999 |
| RU | 2230728 | 12/1999 |
| WO | WO9733850 | 9/1997 |
| WO | WO2007014959 | 2/2007 |

* cited by examiner

*Primary Examiner* — Johann R Richter
*Assistant Examiner* — Pancham Bakshi

(57) ABSTRACT

A process for the preparation of an alkylene glycol, said process comprising contacting an alkylene oxide with carbon dioxide and water in the presence of a catalytic composition comprising an active anion, selected from the group consisting of metalates, carbonate, bicarbonate and hydroxide, immobilized on a first solid support having one or more electropositive sites and a halide immobilized on the first or a second solid support having one or more electropositive sites.

18 Claims, No Drawings

PROCESS FOR THE PREPARATION OF ALKYLENE GLYCOLS

REFERENCE TO PRIOR APPLICATIONS

This application claims the benefit of European Patent Application No. 07112862.3, filed on Jul. 20, 2007, which is incorporated herein by reference in its entirety.

FIELD OF THE INVENTION

The present invention relates to a process for the catalytic conversion of alkylene oxides to alkylene glycols.

BACKGROUND OF THE INVENTION

Alkylene glycols, in particular monoalkylene glycols, are of established commercial interest. For example, monoalkylene glycols are used in anti-freeze compositions, as solvents and as base materials in the production of polyalkylene terephthalates e.g. for fibres or bottles.

The production of alkylene glycols by liquid phase hydrolysis of alkylene oxide is known. The hydrolysis is generally performed by adding a large excess of water, e.g. 20 to 25 moles of water per mole of alkylene oxide. The reaction is considered to be a nucleophilic substitution reaction, whereby opening of the alkylene oxide ring occurs, water acting as the nucleophile. Because the primarily formed monoalkylene glycol also acts as a nucleophile, as a rule a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product.

Catalytic processes, promoting a higher selectivity to monoalkylene glycol product at reduced water levels are known (e.g. EP 0156449, U.S. Pat. No. 4,982,021, U.S. Pat. No. 5,488,184, U.S. Pat. No. 6,153,801 and U.S. Pat. No. 6,124,508). Such catalysts often comprise a strongly basic (anionic) exchange resin, often with quaternary ammonium or quaternary phosphonium electropositive complexing sites, coordinated with one or more anions.

Further examples of catalytic processes known for the reaction of alkylene oxides to alkylene glycols are given in JP 2001151713 and JP 2001151711, wherein a catalytic composition comprising a halide ion and a bicarbonate ion is used to convert an alkylene oxide to the corresponding alkylene glycol in the presence of carbon dioxide and water.

JP 56092228 is directed to the use of molybdenum and/or tungsten as a catalyst for the conversion of alkylene oxide to alkylene glycol, again in the presence of carbon dioxide and water.

The conversion of alkylene oxides to alkylene glycols using a halogen type anion exchange material as the reaction catalyst is disclosed in JP 57139026.

WO 97/33850 describes a catalytic process wherein alkylene oxide is hydrolysed in the presence of carbon dioxide and/or carbon acid salts, and the catalyst is based on an ion exchange polymer material having electropositive sites and in bicarbonate form.

U.S. Pat. No. 4,307,256 describes the reaction of alkylene oxides with water and carbon dioxide in the presence of a tertiary amine catalyst for the production of alkylene glycols. In U.S. Pat. No. 4,160,116 a similar system is described, wherein the catalyst used is a quaternary phosphonium salt.

WO 2007014959 is directed to a process for the conversion of an alkylene oxide to the corresponding alkylene glycol in the presence of a catalytic composition, carbon dioxide and water, wherein the catalytic composition comprises a halide, a metalate, and optionally a macrocyclic chelating compound.

EP 1034158 is directed to the use of a catalytic composition comprising a macrocyclic chelating compound complexed with an ionic compound selected from the group comprising halogenides, carboxylates, hydrogen carbonates, hydrogen sulphites, hydrogen phosphates and metalates, for the hydrolysis of alkylene oxides to alkylene glycols.

In addition, processes for the production of alkylene glycols from alkylene oxides, comprising a two-step process, have been described in the art. Such processes involve the reaction of alkylene oxides with carbon dioxide in the presence of a catalyst, followed by subsequent thermal or catalytic hydrolysis of the resultant alkylene carbonate. Examples of such two-step processes include those described in JP 57106631 and JP 59013741.

Catalysts suitable for the hydrolysis of alkylene carbonates are described in U.S. Pat. No. 4,283,580, which is directed to the use of molybdenum or tungsten in metal or compound form as catalysts in the production of substituted or unsubstituted ethylene glycols by the reaction of substituted or unsubstituted ethylene carbonates with water.

Although progress has been made in methods for the transformation of alkylene oxides into the equivalent alkylene glycols, there still remains a need for new processes with high levels of conversion using highly active and selective catalyst compositions and for catalyst systems that allow easy purification of the desired product.

SUMMARY OF THE INVENTION

According to the present invention, there is provided a process for the preparation of an alkylene glycol, said process comprising contacting an alkylene oxide with carbon dioxide and water in the presence of a catalytic composition comprising an active anion, selected from the group consisting of metalates, carbonate, bicarbonate and hydroxide, immobilised on a first solid support having one or more electropositive sites and a halide immobilised on the first or a second solid support having one or more electropositive sites.

DETAILED DESCRIPTION OF THE INVENTION

It has now surprisingly been found that the conversion of alkylene oxides to the corresponding alkylene glycol can be efficiently catalysed by a catalytic composition comprising an active anion, selected from the group consisting of metalates, carbonate, bicarbonate and hydroxide, immobilised on a solid support and a halide immobilised on either the same or a different solid support.

This heterogeneous system allows for facile separation of the desired product from the catalytic composition. Such separation can be accomplished without distilling of the product in the presence of the catalyst composition at the high temperatures generally required to purify alkylene glycols. The avoidance of separation steps using high temperatures will lead to a lower level of catalyst degradation than may occur in a homogeneous process and will also result in a decrease in (or absence of) by-product formation during the heat treatment (distillation). Further, a higher concentration of catalyst per mole of alkylene oxide may be present at any single point in the reactor in comparison to a homogeneous process, without using extra catalyst.

Furthermore, this heterogeneous catalyst system displays high levels of activity and selectivity in the conversion of alkylene oxides to alkylene glycols.

The alkylene oxides used as starting material in the process of the invention have their conventional definition, i.e. they are compounds having a vicinal oxide (epoxy) group in their molecules.

Particularly suitable are alkylene oxides of the general formula (I),

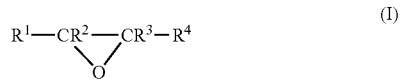

wherein $R^1$ to $R^4$ independently represent a hydrogen atom or an optionally substituted, alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$-$C_3$ alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane and 2,3-epoxybutane. In the present invention, the most preferred alkylene oxide is ethylene oxide.

The preparation of alkylene oxides is well known to the skilled person. In the case of ethylene oxide, it may be prepared by the well known direct oxidation of ethylene, i.e. by air or oxygen oxidation, utilizing silver-based catalysts and often also organic moderators, e.g. organic halides (see for example Kirk Othmer's Encyclopedia of Chemical Technology, $4^{th}$ edition, Vol. 9, pages 923-940).

In the present invention, the active anion is selected from the group consisting of metalates, carbonate, bicarbonate and hydroxide. Preferably, the active anion is a metalate.

As used herein, the term 'metalate' is defined as a metal oxide anion in which the metal is polyvalent, having a positive functional oxidation state of at least +3, and may, for example, be a transition metal. In the present invention, the metalate is suitably selected from metal oxide anions comprising group 5 and 6 metals (according to IUPAC Nomenclature of Inorganic Chemistry, Recommendations 1990. Blackwell Scientific Publications, 1990. Edited by G J Leigh). Preferably, the metalate is selected from the group of tungstates, vanadates and molybdates. Most preferably, the metalate is a molybdate.

Typical examples of such metalate anions include anions conventionally characterized by the formulae $[MoO_4]^{2-}$, $[VO_3]^-$, $[V_2O_7H]^{3-}$, $[V_2O_7]^{4-}$ and $[WO_4]^{2-}$. It is recognized that the chemistry of these metalate anions is complex and the exact chemical formula under the conditions of the process of the present invention may prove to be different, but the above is the commonly accepted characterization.

When the process of the present invention is carried out as a batch process, the amount of active anion, selected from the group consisting of metalates, carbonate, bicarbonate and hydroxide, used in the process of the present invention is suitably in the range of from 0.0001 to 0.5 mol/mol alkylene oxide. Preferably, the active anion, selected from the group consisting of metalates, carbonate, bicarbonate and hydroxide, is present in an amount in the range of from 0.001 to 0.1 mol/mol alkylene oxide.

In a preferred embodiment, the process of the present invention is carried out as a continuous process and the alkylene oxide, carbon dioxide and water are passed over the catalyst as a continuous stream. It will be apparent to the skilled person that, in this embodiment, the amount of active anion present per mole of alkylene oxide at any one point of the process will vary depending on reaction conditions, flow rate, position, etc.

The term halide refers to a compound comprising an anion of one of the elements of group 17 of the periodic table (according to IUPAC Nomenclature of Inorganic Chemistry, Recommendations 1990. Blackwell Scientific Publications, 1990. Edited by G J Leigh). Preferably, the halide is selected from the group of chlorides, bromides and iodides. Most preferably, the halide is an iodide.

When the process of the present invention is carried out as a batch process the amount of halide used in the process of the present invention is suitably in the range of from 0.0001 to 0.5 mol/mol alkylene oxide. Preferably, the halide is present in an amount in the range of from 0.001 to 0.1 mol/mol alkylene oxide.

In a preferred embodiment, the process of the present invention is carried out as a continuous process and the alkylene oxide, carbon dioxide and water are passed over the catalyst as a continuous stream. It will be apparent to the skilled person that, in this embodiment, the amount of halide present per mole of alkylene oxide at any one point of the process will vary depending on reaction conditions, flow rate, position, etc.

The first and second solid supports are supports having one or more electropositive sites. The electropositive site is typically a cation. Suitable solid supports having one or more electropositive sites include those of an inorganic nature such as carbon, silica, silica-alumina, zeolites, glass and clays such as hydrotalcite. Such solid supports may have the cation bonded by adsorption, reaction or grafting. Further, immobilised complexing macrocycles, such as crown ethers, are also considered as solid support having one or more electropositive sites according to this invention, since these materials are able to bind a cation. Preferably, the first and/or second solid support contains a quaternary ammonium, quaternary phosphonium, quaternary arsenonium, quaternary stibonium, a ternary sulfonium cation or a complexing macrocycle. More preferably, the cation is a quaternary ammonium or quaternary phosphonium ion.

Advantageously, in the present invention, solid supports comprising a strongly basic ion exchange resin are used as the first and/or second solid support, wherein the cation is attached to a polymeric backbone. The polymeric backbone may comprise high molecular weight polymers and co-polymers including polyalkylene, polyester, polycarbonate, polyurethane, formaldehyde resins, etc. Suitable commercially available ion exchange resins include those comprising polyacrylate or styrene-divinylbenzene copolymers as polymeric backbones. Resins with silica-based polymeric backbones, such as polysiloxanes, and resins incorporating vinylpyridine monomers in their polymeric backbones may also be used. Commercially available ion exchange resins suitable for the process of the present invention include, but are not limited to, LEWATIT 500 KR (LEWATIT is a trade mark), AMBER-LITE IRA-900, AMBERLITE IRA-458 (AMBERLITE is a trade mark), AMBERJET 4200, AMBERJET 4400 (AMBERJET is a trade mark), DOWEX 1×16 (DOWEX is a trade mark), REILLEX HPQ (REILLEX is a trade mark), MARATHON-A, MARATHON-MSA (MARATHON is a trade mark) and DELOXAN AMP (DELOXAN is a trade mark). Other suitable ion exchange resins include those made according to the method described by Nishikubo, et al. in *J. Polym. Sci., Part A: Polym. Chem.*, (1993) 31, 939-947. These resins have so-called spacer groups, comprising a chemical structure linking the polymeric backbone to the cation. Suitably, the spacer group contains an alkylene group, optionally interrupted with one or more oxygen atoms.

The halide and the active anion, selected from the group consisting of metalates, carbonate, bicarbonate and hydroxide may be supported on solid supports comprising the same or different materials. Preferably, the solid support on which the halide is supported and the solid support on which the active anion, selected from the group consisting of metalates, carbonate, bicarbonate and hydroxide, is supported are formed of the same material.

Both the halide and the active anion, selected from the group consisting of metalates, carbonate, bicarbonate and hydroxide, can independently be immobilised on the solid support or supports by any technique known to the person skilled in the art. These techniques include pore volume impregnation, impregnation, precipitation and ion-exchange. Preferably, the halide and the active anion, selected from the group consisting of metalates, carbonate, bicarbonate and hydroxide, are immobilised on the solid support or supports via ion-exchange. Ion exchange comprises contacting the solid support with a solution, preferably an aqueous solution of a corresponding halide salt and/or a salt of the active anion, selected from the group consisting of metalates, carbonate, bicarbonate and hydroxide, wherein the molar ratio between the halide anion or the active anion, selected from the group consisting of metalates, carbonate, bicarbonate and hydroxide, in the solution and the number of electropositive sites present in or on the solid support is equal to or larger than 0.2. Preferably, the molar ratio between the halide anion or the active anion, selected from the group consisting of metalates, carbonate, bicarbonate and hydroxide, and the number of electropositive sites is between 0.25 and 20. An electropositive site is a site where theoretically an anion can be adsorbed. In the preferred case of the strongly basic ion exchange resins, containing a quaternary ammonium or quaternary phosphonium ion, two such electropositive sites are needed to adsorb the preferred metalate anion $[MoO_4]^{2-}$. Preferably, ion-exchange takes place at a temperature in the range from 0° C. to 100° C., more preferably at a range from 20° C. to 90° C. Preferably, ion-exchange takes place at atmospheric pressure.

The mixture of the active anion, selected from the group consisting of metalates, carbonate, bicarbonate and hydroxide, immobilised on a solid support and the halide ion immobilised on a solid support may be formed as a physical mixture of in the range of from 10 to 90 mol %, preferably in the range of from 20 to 80 mol %, (based on the mixture) of the active anion, selected from the group consisting of metalates, carbonate, bicarbonate and hydroxide, immobilised on a solid support mixed with in the range of from 10 to 90 mol %, preferably in the range of from 20 to 80 mol %, (based on the mixture) of the halide immobilised on a solid support.

Alternatively, the mixture of the active anion, selected from the group consisting of metalates, carbonate, bicarbonate and hydroxide, immobilised on a solid support and the halide immobilised on a solid support may be formed by supporting a suitable amount of the halide on a solid support and then supporting a suitable amount of the active anion, selected from the group consisting of metalates, carbonate, bicarbonate and hydroxide, on the solid support such that the resultant mixture comprises in the range of from 10 to 90 mol % (based on the mixture) of the active anion, selected from the group consisting of metalates, carbonate, bicarbonate and hydroxide, immobilised on the solid support and in the range of from 10 to 90 mol % (based on the mixture) of the halide immobilised on the solid support.

In one particularly preferred embodiment of the present invention, the catalytic composition is formed by reacting a hydroxide form ion exchange resin with in the range of from 10 to 90% of an equivalent of hydrogen halide and then reacting the resultant mixture with in the range of from 10 to 90% of an equivalent of molybdic acid.

The reactions to attach the halide ion and the active anion, selected from the group consisting of metalates, carbonate, bicarbonate and hydroxide, on the solid support may be carried out in the reactor before the addition of the alkylene oxide or, alternatively, it may be carried out before addition of the supported catalytic composition to the reactor.

The amount of water present is usually at least 0.2 mol/mol alkylene oxide present in the reaction mixture, preferably at least 0.5 mol/mol alkylene oxide. An amount of water present of at least 1 mol/mol alkylene oxide is most preferred. Preferably, the amount of water present is less than 25 mol/mol alkylene oxide, more preferably less than 15 mol/mol alkylene oxide. An amount of water present of at most 5 mol/mol alkylene oxide is most preferred.

A benefit of the present invention is that it is possible to carry out the process with high levels of activity and selectivity in the presence of a close to stoichiometric amount of water with respect to alkylene oxide, for example with an amount of water in the range of from 1 mol/mol alkylene oxide to 1.3 mol/mol alkylene oxide, especially with an amount of water of 1 mol/mol alkylene oxide or 1.1 mol/mol alkylene oxide. This reduces the amount of energy required for the removal of excess water from the reaction product.

The water present in the reaction mixture of the present invention may be added to the reaction mixture separately from the alkylene oxide. Alternatively, the alkylene oxide and water may be pre-mixed before being supplied to the reactor. In a preferred embodiment of the invention, an alkylene oxide product mixture from an alkylene oxide reactor is used either without further process steps or after some concentration in a stripper. Most preferably, an ethylene oxide/water mixture, formed by absorption of the product stream from a direct oxidation ethylene oxide reactor is used. This method has a further benefit that the energy expended in isolating the alkylene oxide, prior to the process of the invention, is reduced.

Preferably, the total amount of carbon dioxide supplied to the reactor is in an amount of at least 0.5 mol/mol alkylene oxide, preferably at least 1 mol/mol alkylene oxide. Preferably, the total amount of carbon dioxide supplied to the reactor is an amount of at most 100 mol/mol alkylene oxide, more preferably an amount of at most 10 mol/mol alkylene oxide.

The process of the present invention may be carried out in batch operation. However, in particular for large-scale embodiments, it is preferred to operate the process continuously.

Such continuous process can be carried out in fixed bed reactors, operated in up-flow or down-flow. Other reactor options include bubble column reactors and fluidized bed reactors.

The reactors of the present invention may be maintained under isothermal, adiabatic or hybrid conditions. Isothermal reactors are generally shell- and tube reactors, mostly of the multi-tubular type, wherein the tubes contain the catalyst and a coolant passes outside the tubes. Adiabatic reactors are not cooled, and the product stream leaving them may be cooled in a separate heat exchanger.

It may be advantageous for the process of this invention to recycle a part of the reactor output to at least one inlet of the same reactor, because any temperature difference that may arise between the top and the bottom of the reactor is minimised. Accordingly, less external temperature control is required to maintain the reaction temperature than with a conventional reactor. This is particularly advantageous when isothermal conditions are preferred. The part of the reactor output to be recycled may be conveniently separated from the part not to be recycled after the reactor output has left the reactor; or alternatively the part of the reactor output to be recycled may be conveniently removed from the reactor via a different outlet of the reactor than that from which the part of the reactor output not to be recycled is removed. The amount of reactor output mixture to be recycled may be varied to obtain optimum performance with regard to other reaction parameters employed.

In order to accommodate any swelling of the catalyst that may occur during operation, the reactor volume can advantageously be greater than the volume occupied by the catalyst therein, for example in the range of from 10 to 70 vol % greater.

Suitable reaction temperatures for the catalytic preparation of alkylene glycols, according to the current invention are generally in the range of from 40 to 200° C., whereby temperatures in the range of from 50 to 120° C. are preferred.

The reaction pressure is usually selected in the range of from 100 to 5000 kPa, preferably in the range of from 200 to 3000 kPa, most preferably in the range of from 500 to 2000 kPa.

A problem, which may occasionally arise in certain processes using catalysts containing the above mentioned quaternary or ternary groups, is the presence of small amounts of impurities in the product stream. For example, when strongly basic anion exchange resins, wherein the basic groups comprise quaternary ammonium or phosphonium groups, are used as the solid support for the catalytic group it has been found that during operation, small amounts of amines or phosphines tend to leach from the resin into the product stream. Other impurities in the product stream may include amines originating from corrosion inhibitors, which may be added to the water used in the process. Although the amounts of such contaminants reaching the end-product are generally very small, they may affect the quality of the end-product such that it may be desirable to reduce the amounts to as low as possible so as not to affect the quality of the product. For example, trimethylamine (TMA) and/or dimethylamine (DMA) may reach the end product in an amount of up to 10 ppm while the fishy odour of TMA may be detected in an amount as low as 1 ppb.

An effective measure in removing such contaminants is the use of a post-reactor bed, containing an acidic species, particularly a strongly acidic ion exchange resin, which effectively captures the contaminants. Strongly acidic ion exchange resins may be of the sulfonic type. Commercially available examples are those known by the trademarks AMBERLYST 15, AMBERJET 1500H, AMBERJET 1200H, DOWEX MSC-1, DOWEX 50W, DIANON SK1B, LEWATIT VP OC 1812, LEWATIT S100 MB and LEWATIT S 100 G1. Such strongly acidic ion exchange resins are available in $H^+$ form and in salt form, such as the $Na^+$ form. When only the $H^+$ form of the strongly acidic resin is used in the post-reactor guard bed, the product stream after passing it may become acidic. Using a mixture of the strongly acidic ion exchange resin in its $H^+$ form and salt form has the advantage of the pH of the product stream remaining close to neutral.

Such a post-reactor bed may be positioned after the reactor or series of reactors in which the process according to the present reaction is carried out. An added advantage of the strongly acidic post-reactor bed positioned after a reactor bed in which the alkylene oxide has undergone conversion to form the corresponding alkylene glycol is that any remaining alkylene oxide, which may be still present in the product alkylene glycol product stream, is converted to alkylene glycol.

In order to allow for exhaustion and replacement or regeneration of the strongly acidic ion exchange resin during operation, it is advantageous to operate the post-reactor bed in two or more separate vessels, to allow the process to be switched between the two vessels, thus maintaining continuous operation.

Exhausted strongly acidic ion exchange resin can be regenerated by treatment with an acid, such as HCl and $H_2SO_4$. Hot sulfuric acid of 0.1 to 2 N has been proven to be effective.

The following non-limiting Examples will illustrate the invention.

EXAMPLES

Molybdate Catalyst Preparation

AMBERJET 4200 resin (ex Rohm & Haas; chloride form), based on a polystyrene/divinylbenzene copolymer backbone, was used in the following examples for the molybdate catalyst. 100 ml of wet AMBERJET 4200 (i.e. a commercial sample containing 55% of water) was transferred onto a vertical glass ion-exchange column and treated with 1100 ml of a 3% molybdate ($Na_2MoO_4$) solution with a temperature of 75-80° C. with an LHSV of 0.6 l/l/h. Finally, rinsing was carried out with 1000 ml demineralised water at room temperature (LHSV 0.6 l/l/h).

Iodide Catalyst Preparation

For the iodide catalyst, LEWATIT M500KR (ex Bayer; hydroxide form) was used. Approximately 40 g of the commercially supplied ion exchange resin (in the OH form) in 100 ml of water was stirred with approximately 15 g of an approximately 50% aqueous HI solution for 2 hours. The resulting resin was filtered and then washed with water until the wash water was free of HI (i.e. when the wash water had a pH greater than 5).

All ion exchange resin solid supports were dried in a vacuum oven overnight (80° C., 200-250 mm Hg)

General Reaction Conditions

The reactor was filled with water and the ion exchange resin-supported halide (if present) was added in a sufficient quantity to provide a concentration of halide ions of 0.12 mol/l, and the ion exchange resin supported metalate (if present) was added in a sufficient quantity to provide a concentration of 0.025 mol/l. The reactor was then purged with $CO_2$ and pressurised with a $CO_2$ atmosphere of approximately 5 bar (500 kPa). The reactor content was then heated to 90° C. and the reactor was further pressurised to 20 bar (2,000 kPa). The ethylene oxide was then pumped into the reactor at a rate of 6.3 g/min until a water/EO ratio of 4.02 mol/mol was reached. These conditions result in a halide concentration (if present) of 0.0118 mol/mol ethylene oxide and a metalate concentration (if present) of 0.0035 mol/mol ethylene oxide. The reactor content was maintained at the appropriate temperature and pressure (by the continuous supply of $CO_2$) and samples were taken, and analysed by gas liquid chromatography (GLC). The results are shown in Table 1.

TABLE 1

| | IER I⁻ present | IER molybdate present | Conversion* EO (%) | Selectivity | | | T (min) | TOF** (h⁻¹) |
|---|---|---|---|---|---|---|---|---|
| | | | | EC | MEG | Total | | |
| 1 | NO | NO | 39.9 | 0.0 | 62.4 | 62.4 | 307 | — |
| 2 | NO | YES | 20.0 | 0.0 | 66.1 | 66.1 | 1335 | — |
| 3 | YES | NO | 82.1 | 76.5 | 21.6 | 98.1 | 219 | 51 |
| 4 | YES | YES | 85.8 | 2.2 | 95.9 | 98.0 | 360 | 53 |

*EO Conversion measured after 1 h;
**TOF = turn over frequency (moles of EC + moles of MEG produced per mole of iodide catalyst per hour)

These Examples demonstrate that the catalysts of the present invention display high levels of activity and selectivity when used in the transformation of an alkylene oxide to the corresponding alkylene glycol. The use of a heterogeneous catalyst allows facile separation of the desired product without the need for a distillation step, which might lead to the decomposition of the product.

What is claimed is:

1. A process for the preparation of an alkylene glycol, said process comprising continuously passing an alkylene oxide, carbon dioxide and water over a catalytic composition comprising an active anion, selected from the group consisting of metalates, carbonate, bicarbonate and hydroxide, immobilized on a first solid support having one or more electropositive sites and a halide immobilized on the first or a second solid support having one or more electropositive sites, wherein the carbon dioxide is added in an amount of at least 0.5 mol/mol alkylene oxide.

2. The process as claimed in claim 1, wherein the halide is an iodide.

3. The process as claimed in claim 1, wherein the active anion is a metalate selected from the group consisting of molybdates, vanadates and tungstates.

4. The process as claimed in claim 1, wherein the metalate is a molybdate.

5. The process as claimed in claim 1, wherein the active anion is selected from the group consisting of carbonate, bicarbonate and hydroxide.

6. The process as claimed in claim 1, wherein the first and/or second solid support contains a quaternary ammonium, quaternary phosphonium, quaternary arsenonium, quaternary stibonium or a ternary sulfonium cation.

7. The process as claimed in claim 1, wherein the first and/or second solid support contains a quaternary ammonium or quaternary phosphonium cation.

8. The process as claimed in claim 1, wherein the active anion and the halide are immobilized on the same type of solid support material.

9. The process as claimed in claim 1, wherein the solid support comprises a strongly basic ion exchange resin selected from the group consisting of a polyacrylate polymer or a styrene-divinylbenzene copolymer.

10. The process as claimed in claim 1, wherein the catalytic composition is prepared by reacting a hydroxide form ion exchange resin with hydrogen halide and then reacting the resultant mixture with molybdic acid.

11. The process as claimed in claim 1, wherein the water is present in the range of from 0.2 to 25 mol/mol alkylene oxide present in the reaction mixture.

12. The process as claimed in claim 1, wherein the water is present in the range of from 0.5 to less than 15 mol/mol alkylene oxide present in the reaction mixture.

13. The process as claimed in claim 1, wherein the water is present in the range of from 0.5 to 5 mol/mol alkylene oxide present in the reaction mixture.

14. The process as claimed in claim 1, wherein the total amount of carbon dioxide supplied to the reactor is in an amount in the range of from 0.5 to 100 mol/mol alkylene oxide.

15. The process as claimed in claim 1, wherein the total amount of carbon dioxide supplied to the reactor is in an amount in the range of from 1 to 10 mol/mol alkylene oxide.

16. The process as claimed in claim 1, wherein the alkylene oxide is ethylene oxide.

17. The process as claimed in claim 16, wherein an ethylene oxide/water mixture, formed by absorption of an ethylene oxide product stream from a direct oxidation ethylene oxide reactor, is contacted with the catalytic composition.

18. A process for the preparation of ethylene glycol, said process comprising continuously passing ethylene oxide, carbon dioxide and water over a catalytic composition comprising a molybdate anion immobilized on a first solid support having one or more electropositive sites and an iodide anion immobilized on the first or a second solid support having one or more electropositive sites, wherein the carbon dioxide is added in an amount of at least 0.5 mol/mol alkylene oxide.

* * * * *